United States Patent

Suyama et al.

[11] Patent Number: 5,125,959
[45] Date of Patent: Jun. 30, 1992

[54] METHOD OF THINNING LATERAL FLOWERS OF APPLES

[75] Inventors: Toshihisa Suyama, Ryugasaki; Kiyoshi Yokota, Morioka; Shozo Kato, Fujisawa, all of Japan

[73] Assignee: Tokuyama Soda Kabushiki Kaisha, Tokuyama, Japan

[21] Appl. No.: 651,952

[22] Filed: Feb. 7, 1991

[51] Int. Cl.$^5$ .................... A01N 43/40; A01N 43/56
[52] U.S. Cl. ........................... 71/92; 71/65
[58] Field of Search ............................. 71/92

[56] References Cited

U.S. PATENT DOCUMENTS 4,193,788  3/1980  Shudo et al. .................... 71/94
4,613,359  9/1986  Yamazaki et al. ................ 71/122
4,789,398  12/1988  Yamazaki et al. ................ 71/122

FOREIGN PATENT DOCUMENTS 62-153283  7/1987  Japan.
63-174905  7/1988  Japan.

OTHER PUBLICATIONS

Knight et al., in *CAS* 107:2611b "Chemical Thinning of the Apple Cultivar Spartan", J. Hortic. Sci. 62(2):135-139, 1987.

*Primary Examiner*—Richard L. Raymond
*Assistant Examiner*—S. Mark Clardy
*Attorney, Agent, or Firm*—Sherman and Shalloway

[57] ABSTRACT

A method of thinning lateral flowers of apples, comprising applying of flower thinning effective amount of a pyrazole compound represented by general formula (I)

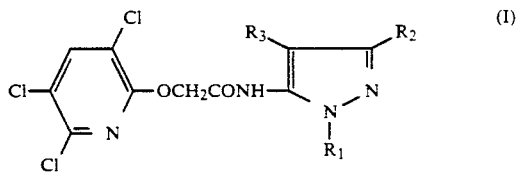

wherein
  $R_1$ represents an alkyl group having 1 to 4 carbon atoms; and
  $R_2$ and $R_3$, which are the same or different, each represent a hydrogen atom or an alkyl group having 1 to 4 carbon atoms,
to flowers of apples. A compound in which $R_1$ and $R_2$ are each a methyl group, and $R_3$ is a hydrogen atom is preferred. The pyrazole compounds are applied at a flowering stage of apples, preferably in a period from immediately after full bloom to terminal flowers of apples to 2 days thereafter, typically in a proportion of from about 5 mg to about 75 g per tree at a coverage in a range of from about 20 mg/10a to about 2,000 g/10a.

8 Claims, No Drawings

METHOD OF THINNING LATERAL FLOWERS OF APPLES

The present invention relates to a method of thinning lateral flowers of apples using certain types of specified pyrazole compounds.

When left to stand as they are under natural conditions after their flowering and pollination, many fruit trees will retain most fruits on their branches, resulting in that fruit size and fruit quality tend to decrease as well as heavy load is posed on the trees to reduce the tree vigor. In order to solve these problems, fruit thinning has been performed by hand. With view to reducing man-power, it has been a recent trend to use certain types of chemicals for fruit thinning. Examples of such chemicals include flower thinning agents which are used to treat fruit trees therewith during flowering period so that only necessary amount of flowers can mature into fruit, and fruit thinning agents which are used to treat the trees therewith at an appropriate timing after their fruit bearing to drop excessive fruits. In particular, flower thinning agents which may be used during flowering period are more important than other chemical agents because they can maximally reduce the load to be imposed on trees for growing excessive fruits.

Heretofore, many compounds have been reported which have a flower thinning activity of a fruit thinning activity. However, only a part of them has been used practically in spite of their importance. In addition, appropriate chemicals must be selected depending on the variety of fruit trees and it is rarely the case that a single chemical is commonly used as a fruit thinning agent or a flower thinning agent for over a wide range in kind or species or variety of fruit trees. For example, attempts to use a chemical known to be useful as a fruit thinning agent for mandarin oranges in order to thin flowers of apples will in most cases fail to exhibit adequate effects because the effect of the chemical will fluctuate widely. Even if the chemical was effective on apples, the leaves of apples have epidermal components which differ from the epidermal components of the leaves of mandarin oranges and in fact the former are more susceptible to chemicals than the latter. From this it follows that the leaves of apples tend to suffer from leaf wilting, suppression and malformation more readily than the leaves of mandarin oranges. The flower thinning agents for apples must meet severe requirements that they must act on the trees treated therewith such that they will bear from five to six flowers in a single cluster but lateral flowers will be selectively thinned with retaining a terminal flower (or king blossom) that bears good fruit. Therefore, only a very limited number of chemicals can be used as a flower thinning agent for apples.

Typical example of the flower thinning agent now used in practice include lime sulfur combination and calcium alkylbenzenesulfonates. The lime sulfur combination is disadvantageous not only in that it must be used from three to four times during flowering period because it exhibits no constant effect and the duration of their effect is rather short, which is very trouble-some to growers, but also in that it causes chemical injury such as leaf browning, and also it is disadvantageous in that when bee honey is contaminated therewith, the honey smells badly due to the presence of sulfur. On the other hand, the calcium alkylbenzenesulfonates are also disadvantageous in many respects. For example, they are disadvantageous in that their effect is unstable, their activity is low, and they cause chemical injury such as "rusts" in fruits after the treatment therewith.

The lime sulfur combination and calcium alkylbenzenesulfonate are flower thinning agents for apples which are currently used in Japan. On the other hand, in U.S.A. DNOC (trade name: Egletol) has been used as a flower thinning agent for apples until a recent date. However, this chemical is now used little in practice because of its strong toxicity.

While the present inventors have already proposed some pyrazole compounds useful as a herbicide, fungicide or flower thinning agent for mandarin oranges (cf. Japanese Patent Publications (Kokai) Nos. Sho 62-153283 and Sho 63-174905), they have now found that a very limited members among the above-described pyrazole compounds having a specified chemical structure have a flower thinning activity for selectively thinning lateral flowers of apples without causing chemical injury to fruits and leaves of apples and the compounds are practically very useful as a flower thinning agent for apples Accordingly, the present invention provides a method of thinning lateral flowers of apples, comprising applying a thinning effective amount of a pyrazole compound represented by general formula (I)

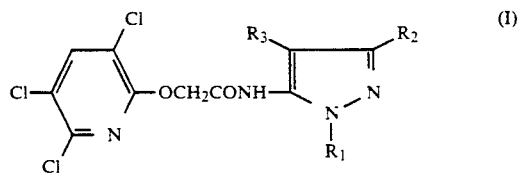

wherein $R_1$ represents an alkyl group having 1 to 4 carbon atoms; and $R_2$ and $R_3$, which are the same or different, each represent a hydrogen atom or an alkyl group having 1 to 4 carbon atoms, to flowers of apples.

The compounds of the general formula (I) above have excellent thinning characteristics for flower thinning of apples because they exhibit a thinning activity selectively on lateral flowers of apples but give substantially no effect on terminal flowers of apples. In addition, the compounds of the general formula (I) have a unique feature that they are effective for increasing yield of fruit crops, increasing sugar content and preventing fruit abscission in preharvest stages and therefore they are practically suitable as a flower thinning agent for apples.

The "alkyl group having 1 to 4 carbon atoms" represented by $R_1$, $R_2$ and/or $R_3$ may be of a straight chain or branched chain, and examples thereof include a methyl group, an ethyl group, an n-propyl group, an isopropyl group, an n-butyl group, an isobutyl group, a sec-butyl group, a tert-butyl group, etc.

In the general formula (I) above, $R_2$ and $R_3$, independently, may be a hydrogen atom or an alkyl group having 1 to 4 carbon atoms. Generally, it is preferred that $R_2$ be an alkyl group having 1 to 4 carbon atoms, particularly a methyl group, and $R_3$ be a hydrogen atom. Among the compounds, most preferred is a compound of the general formula (I) in which $R_1$ and $R_2$ are each a methyl group and $R_3$ is a hydrogen atom.

Specific examples of the general formula (I) include the following compounds:

α-(3,5,6-Trichloro-2-pyridyloxy)-N-(1',3'-dimethyl-5'-pyrazolyl)acetamide;

α-(3,5,6-Trichloro-2-pyridyloxy)-N-(1'-ethyl-3'-methyl-5'-pyrazolyl)acetamide;

α-(3,5,6-Trichloro-2-pyridyloxy)-N-(1'-propyl-3'-methyl-5'-pyrazolyl)acetamide;

α-(3,5,6-Trichloro-2-pyridyloxy)-N-(1'-isopropyl-3'-methyl-5'-pyrazolyl)acetamide;

α-(3,5,6-Trichloro-2-pyridyloxy)-N-(1'-butyl-3'-methyl-5'-pyrazolyl)acetamide;

α-(3,5,6-Trichloro-2-pyridyloxy)-N-(1'-isobutyl-3'-methyl-5'-pyrazolyl)acetamide;

α-(3,5,6-Trichloro-2-pyridyloxy)-N-(1'-tertbutyl-3'-methyl-5'-pyrazolyl)acetamide;

α-(2,5,6-Trichloro-2-pyridyloxy)-N-(1',4'-dimethyl-5'-pyrazolyl)acetamide;

α-(3,5,6-Trichloro-2-pyridyloxy)-N-(1'-methyl-5'-pyrazolyl)acetamide;

α-(3,5,6-Trichloro-2-pyridyloxy)-N-(1'-butyl-5'-pyrazolyl)acetamide;

α-(3,5,6-Trichloro-2-pyridyloxy)-N-(1'-methyl-3'-ethyl-5'-pyrazolyl)acetamide; etc.

The compounds of the general formula (I), which are known per se (cf. Japanese Patent Publication (Kokai) No. Sho 62-153283 referred to above), can readily be produced, for example, by reacting a pyrazole derivative of general formula (II)

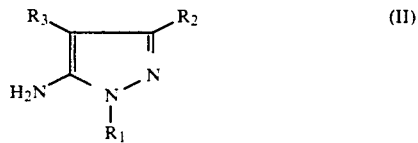

wherein $R_1$, $R_2$ and $R_3$ have the same meanings as defined above, with a carboxylic acid halide of general formula (III)

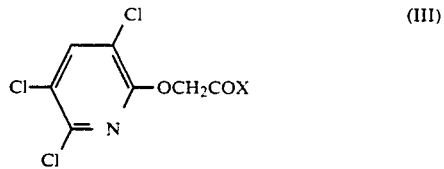

wherein X represents a halogen atom, under ordinary amidation reaction conditions.

The compounds of the general formula (I) may be applied to apple trees during a period from their flowering stage in which the first flower blooms to a stage in which most flowers wither and drop from the trees. However, in order to obtain favorable results, it is convenient to apply them during a period from immediately after full bloom, of terminal flowers to two days thereafter. By the term "full bloom of terminal flowers" referred to herein is meant a timing when 80 % of total terminal flowers on the apple tree concerned are in bloom.

While the amount of the compounds of the general formula (I) to be applied to flowers of apples is difficult to specify because it varies from variety to variety, generally speaking, it may be in a range of from about 5 mg to about 75 g, preferably from about 50 mg to about 15 g, per apple tree (about 2 m in height and about 2.5 m in width). From the viewpoint of cultivation area, it may be a tentative standard that the pyrazole compounds of the general formula (I) be applied at a coverage in a range of from about 20 mg/10a to about 2,000 g/10a, preferably from about 0.2 g/10a to about 400 g/10a. However, their optimal effective amount for flower thinning will vary depending on various factors such as amount of apple flowers, vigor of apple trees, climatic conditions, location of cultivation fields and the like, and growers may make their decision based on their experience taking into consideration such factors. It is also possible for growers to apply the pyrazole compounds of the general formula (I) in amounts outside the above-described ranges if they think different dosages are more appropriate.

When applying the compounds of the formula (I) to apple trees, the compounds may be sprayed in the form of powder, or ordinarily, they are sprayed after being formulated into appropriate formulations together with agriculturally acceptable carrier or diluent and optionally other auxiliary agents.

Type of formulations are not limited particularly and the compounds may be formulated into any known formulations such as powder, coarse powder, fine granule, granule, wettable powder, wettable granule, emulsion, flowable composition, oil suspension and the like.

Suitable solid carriers which can be used upon preparing a flower thinning agent containing one or more of the compounds of the general formula (I) as active ingredient include clays represented by kaolinites, montmorillonites, attapulgites or geikielites; inorganic substances such as talc, mica, pyrophyllite, pumice, vermiculite, gypsum, calcium carbonate, dolomite, diatomaceous earth, magnesium lime, phosphor lime, zeolite, silicic anhydride, and synthetic calcium silicate; vegetative organic substances such as soybean flour, tobacco flour, walnut flour, wheat flour, wood flour, starch, and crystalline cellulose; synthetic or natural high polymers such as cumarone resins, petroleum resins, alkyd resins, polyvinyl chloride, polyalkylene glycol, ketone resins, ester gum, copal gum and dammar gum; and waxes such as carnauba wax and bee wax or urea.

As for liquid carriers, there can be cited, for example, paraffinic or naphthenic hydrocarbons such as kerosene, mineral oil, spindle oil and white oil; aromatic hydrocarbons such as benzene, toluene, xylene, ethylbenzene, cumene and methyl-naphthalene; chlorinated hydrocarbons such as carbon tetrachloride, chloroform, trichloroethylene and monochloro-benzene, o-chlorotoluene; ethers such as dioxane and tetrahydrofuran; ketones such as acetone, methyl ethyl ketone, diisobutyl ketone, cyclohexanone, acetophenone and isophorone; esters such as ethyl acetate, amyl acetate, ethylene glycol acetate, diethylene glycol acetate, dibutyl maleate and diethyl succinate; alcohols such as methanol, n-hexanol, ethylene glycol and diethylene glycol; ether alcohols such as ethylene glycol phenyl ether, diethylene glycol ethyl ether and diethylene glycol butyl ether; polar solvents such as N,N-dimethylformamide and dimethyl sulfoxide or water; and the like.

If desired, the formulations containing one or more of the compounds of the general formula (I) may be compounded with known surfactants for various purposes such as emulsification, dispersion, wetting, mineral dispersion, bonding, disintegration control, stabilization of active ingredients, and improvement of flowability, rust proofing. As for the surfactant, there can be used any type of surfactants among nonionic, cationic, anionic and amphoteric surfactants. Usually, it is preferred to use nonionic surfactants and/or anionic surfactants. Suitable examples of the nonionic surfactants include higher alcohols such as lauryl alcohol, stearyl alcohol and oleyl alcohol; addition polymerization products of an alkylphenol such as isooctylphenol or nonylphenol with ethylene oxide; addition polymerization products of an alkylnaphthol such as butylnaphthol or octylnaphthol with ethylene oxide; addition polymerization products of a higher fatty acid such as palmitic acid, stearic acid or oleic acid with ethylene oxide; addition polymerization products of a monoalkyl or dialkyl phosphate such as stearyl phosphate or dilauryl phosphate with ethylene oxide; addition polymerization products of an amine such as dodecylamine or stearylamine with ethylene oxide; higher fatty acid esters of a polyhydric alcohol such as sorbitan and their addition polymerization products with ethylene oxide; addition polymerization products of ethylene oxide with propylene oxide; esters of a polybasic fatty acid with an alcohol such as dioctyl succinate; and the like. Examples of suitable anionic surfactants include alkyl sulfate salts such as sodium lauryl sulfate and oleyl sulfate amine salt; alkylsulfonates such as sodium dioctyl sulfosuccinate and sodium 2-ethylhexenesulfonate; arylsulfonates such as sodium isopropylnaphthalenesulfonate, sodium salt of parametaldehyde condensate of naphthalenesulfonic acid and sodium ligninsulfonate, sodium dodecylbenzenesulfonate; phosphates such as sodium tripolyphosphate; and the like.

The formulations containing one or more of the compounds of the general formula (I) may be compounded with known auxiliary agents, if desired. As for the auxiliary agents which can be used advantageously in the formulations, there can be cited, for example, casein, gelatin, albumin, hide glue, sodium alginate, carboxymethylcellulose, methylcellulose, hydroxyethylcellulose, polyvinyl alcohol, etc.

Further, the formulations may optionally contain one or more of agriculturally or horticulturally active compounds such as fungicides, insecticides, and plant growth regulators.

The above-described carriers, surfactants and auxiliary agents are used singly or in combination depending on the purpose taking the type and application conditions of the formulations into consideration.

Method of preparing the formulations used in the present invention is not limited particularly and any known method in the art may be used. For example, as a concrete example of the method of preparing wettable powder, a method can be used in which the compound of the general formula (I) is dissolved in an organic solvent, a surfactant and a carrier are added to the resulting solution, the mixture is pulverized and blended well, and then the organic solvent is removed to obtain a wettable powder.

It is desirable to use the compounds of the general formula (I) after formulating them into wettable powder or wettable granule. In this case, the formulations may be used after dilution with water or the like so that the final concentration of the compound or compounds of the general formula (I) is in a range of from about 1 to about 5,000 ppm, preferably from about 10 to about 1,000 ppm.

The chemical liquid diluted to a concentration in the above-described range is sprayed in an amount of generally from about 5 to about 15 liters per apple tree (height: about 2 m, width: about 2.5 m), or from about 20 to 400 liters/10a in terms of coverage of cultivation area.

There is no limitation on the variety of apple trees to which the flower thinning according to the present invention can be applied, and the method of the present invention is applicable to a wide range in variety of apples such as Fuji, Tsugaru, Starking Delicious, Jona Gold, Mutsu, Ourin, Kougyoku, Asahi, Senshu, Red Delicious, Golden Delicious, Glany Smith, Jonathan Rome Beauty, Yellow Newton, Baldwin, Red Delicious, Cortland, Grimes and McIntosh.

The flower thinning agent according to the present invention which contains one or more of the compounds of the general formula (I) as active ingredient (hereafter, referred to as "the flower thinning agent of the present invention") has an excellent flower thinning activity on apples. For example, as will be obvious from the examples described hereinbelow, the flower thinning agent of the present invention considerably reduces ratios of remaining flowers of lateral flowers as compared with control lots which have received no treatment. Thus, it gives substantially no effects on terminal flowers but exhibits a higher effect than is experienced when treating apples with a lime sulfur combination now put on the market in the form of a solution diluted to a practically used concentration of 1/100 time as thick as the stock solution (concentration of stock solution: 11 %), and at the same time, it is very safe because it causes no chemical injury such as leaf browning or leaf malformation as is usually observed when apple trees are treated with lime sulfur combination.

The flower thinning effect on apples of the pyrazole compounds of the general formula (I) according to the present invention is based on different mechanism from that of the conventional flower thinning agents. While the conventional flower thinning agents cause flowers to drop or inhibit the growth of flowers or let flowers wither by giving partial damages thereto, the compounds of the general formula (I) cause lateral flowers to remain on the branches without fructification or, even if having fructified, prevent the fruits from growing and let them be kept in small sizes and allow only terminal flowers to grow normally. This type of flower thinning effect given by the flower thinning agent of the present invention has not been observed with the conventional flower thinning agents and is quite new. Although the mechanism on which its activity is exhibited remains to be clarified yet, this is a major feature of the present invention.

Hereafter, the present invention will be explained in greater detail by way of examples but the present invention should not be construed to be limited thereto.

Preparation of Active Compound

Synthesis Example 1

To a solution of 0.86 g (0.0077 mole) of 5-amino-1,3-dimethylpyrazole in 10 ml of chloroform was added 1.09 ml (0.0078 mole) of triethylamine. To this solution was dropwise added a solution of 2.14 g (0.0078 mole) of 3,5,6-trichloro-2-pyridyloxy-acetyl chloride in 20 ml of chloroform. After stirring the mixture over night, the reaction mixture was washed with water, and the chloroform layer was dried over anhydrous sodium sulfate. After removing chloroform by evaporation, the residue obtained was recrystallized from chloroform-hexane to obtain 2.22 g of colorless solid. As a result of IR, $^1$H-

NMR and MS analyses, the product was confirmed to be -(3,5,6-trichloro-2-pyridyloxy)acetic acid-N-(1',3'-dimethyl-5'-pyrazolyl)amide (Compound No. 1)...

In the same manner as above, Compounds Nos. 2 to 8 as shown in Table 1 below were synthesized.

Formulation of Active Compound

Formulation Example 1 (Wettable Powder)

A mixture of the following:

| | |
|---|---|
| Compound of the general formula (I): | 10 parts by weight |
| Polyoxyethylene nonylphenyl ether: | 2 parts by weight |
| Fine particle clay: | 40 parts by weight |
| Geikielite: | 48 parts by weight | was ground and mixed using a hammer mill to obtain finepowder wettable powder.

Formulation Example 2 (Wettable Granule)

A mixture of the following:

| | |
|---|---|
| Compound No. 1 shown in TABLE 1 below: | 50 parts by weight |
| Clay: | 20 parts by weight |
| White carbon: | 15 parts by weight |
| Sodium dioctylsulfosuccinate: | 5 parts by weight |
| Condensate of naphthalenesulfonic acid with formaldehyde: | 7 parts by weight |
| Sodium carboxymethylcellulose | 3 parts by weight | was ground and mixed, and water was added to the resulting mixture in a proportion of 15 parts by weight of water per 100 parts by weight of the mixture. The mixture thus obtained was granulated using a rolling granulator, followed by drying and sifting to obtain granules of 16 to 42 mesh.

Example 1

A branch bearing about 100 clusters was selected from a 12 year old apple tree (variety: Fuji), and an aqueous dilution (300 ppm) of wettable powder of each compound described in Table 1 was fully sprayed on all over the branch by a hand spray on the next day to the full bloom of terminal flowers. The amount of the solution corresponded to 300 liters/10a.

As the wettable powder, a 10 % wettable powder was used which was prepared by Formulation Example 1.

After 30 days from the application, the flower thinning effects of the respective test compounds were examined and the results obtained are shown in Table 1. Evaluation was expressed in terms of ratio of remaining fruits represented by formula below on both terminal flowers and lateral flowers. Because the ration of remaining fruits is equal to the ration of remaining flowers, the flower thinning effect of a chemical used can be known by comparing the ratio of remaining fruit with that obtained on control (non-treated). As for the chemical injury, results of observation on the conditions of leaves such as leaf abscission, leaf discoloration, leaf malformation of leaves were evaluated based on the following 5-class (- ~ + + +) rating criteria.

$$\text{Ratio of Remaining Fruits} = \frac{\text{Number of Normal Fruits on the Day of Examination}}{\text{Number of Flowers on the Day of Application}} \times 100$$

Chemical Injury:
- −: Normal
- ±: Slight injury
- +: Light injury
- + +: Medium injury
- + + +: Heavy injury

TABLE 1

| No. | Compound | Ratio of Remaining Fruits (%) | | Phytotoxicity |
|---|---|---|---|---|
| | | Lateral Flowers | Terminal Flowers | |
| 1 | Cl-pyridyl(Cl,Cl)-O-CH$_2$CONH-pyrazolyl(CH$_3$, N-CH$_3$) | 3 | 83 | — |
| 2 | Cl-pyridyl(Cl,Cl)-O-CH$_2$CONH-pyrazolyl(CH$_3$, N-C$_2$H$_5$) | 4 | 80 | — |
| 3 | Cl-pyridyl(Cl,Cl)-O-CH$_2$CONH-pyrazolyl(CH$_3$, N-C$_3$H$_7$) | 5 | 78 | — |

TABLE 1-continued

| No. | Compound | Ratio of Remaining Fruits (%) | | Phyto-toxicity |
|---|---|---|---|---|
| | | Lateral Flowers | Terminal Flowers | |
| 4 | ![structure: 3,4,5-trichloropyridin-2-yl-OCH₂CONH-pyrazole with 3-CH₃ and N-C(CH₃)₃] | 8 | 76 | — |
| 5 | ![structure: 3,4,5-trichloropyridin-2-yl-OCH₂CONH-pyrazole with 4-CH₃ and N-CH₃] | 10 | 75 | — |
| 6 | ![structure: 3,4,5-trichloropyridin-2-yl-OCH₂CONH-pyrazole with N-CH₃] | 8 | 81 | — |
| 7 | ![structure: 3,4,5-trichloropyridin-2-yl-OCH₂CONH-pyrazole with C₂H₅ and N-CH₃] | 8 | 78 | — |
| 8 | ![structure: 3,4,5-trichloropyridin-2-yl-OCH₂CONH-pyrazole with N-(CH₂)₃CH₃] | 12 | 77 | — |
| 9 | Control (No Treatment) | 62 | 83 | — |

Comparative Example 1

Apple trees were treated in the same manner as in Example 1 using compounds reported as being useful as a fruit thinning agent for mandarin oranges and similar compounds shown in Table 2. On the other hand, 100 time dilution of 11% lime sulfur combination currently used as a flower thinning agent for apples was applied twice, i.e., after 2 days and 5 days, respectively, counted from the blooming of terminal flowers, and the ratios of remaining fruits and phytotoxicity were examined. Results obtained are shown in Table 2.

TABLE 2

| No. | Comparative Compound | Ratio of Remaining Fruits (%) | | Phyto-toxicity |
|---|---|---|---|---|
| | | Lateral Flowers | Terminal Flowers | |
| 10 | ![structure: 2,4-dichlorophenyl-OCH(phenyl)CONH-pyrazole with CH₃ and N-CH₃] | 45 | 60 | — |

TABLE 2-continued

| No. | Comparative Compound | Ratio of Remaining Fruits (%) | | Phyto-toxicity |
| --- | --- | --- | --- | --- |
| | | Lateral Flowers | Terminal Flowers | |
| 11 | ![compound 11: F, EtO-phenyl-O(CH2)2CH2CONH-pyrazole-Cl, N-CH2CH2CH3] | 37 | 73 | — |
| 12 | ![compound 12: Cl-pyridine-OCH(CH3)CONH-pyrazole(CH3,CH3)] | 28 | 65 | — |
| 13 | ![compound 13: EtOCH2-pyridine-O(CH2)3CH(phenyl)CONH-pyrazole-Et, N-(3,4-dinitrophenyl)] | 45 | 60 | — |
| 14 | ![compound 14: tetrachloropyridine-OCH2COOH] | 37 | 73 | +++ Leaf Malformation Browning |
| 15 | ![compound 15: 2,4-dichlorophenyl-OCH(phenyl)COOC2H5] | 28 | 65 | ++ Leaf Malformation |
| 16 | Lime Sulfur Combination | 39 | 71 | + Browning |

What is claimed is:

1. A method of thinning lateral flowers of apples, comprising applying a flower thinning effective amount of a pyrazole compound represented by general formula (I)

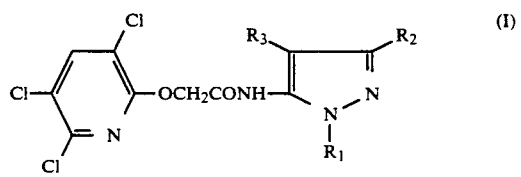

wherein

R₁ represents an alkyl group having 1 to 4 carbon atoms; and

R₂ and R₃, which are the same or different, each represent a hydrogen atom or an alkyl group having 1 to 4 carbon atoms, to flowers of apples.

2. The method as claimed in claim 1, wherein in the general formula (I), $R_2$ is an alkyl group having 1 to 4 carbon atoms, and $R_3$ is a hydrogen atom.

3. The method as claimed in claim 2, wherein $R_2$ is a methyl group.

4. The method as claimed in claim 1, wherein in the general formula (I), $R_1$ and $R_2$ are each a methyl group, and $R_3$ is a hydrogen atom.

5. The method as claimed in claim 1, wherein said pyrazole compound is applied at a flowering stage of said apples.

6. The method as claimed in claim 1, wherein said pyrazole compound is applied in a period from immediately after full bloom of terminal flowers of said apples to 2 days thereafter.

7. The method as claimed in claim 1, wherein said pyrazole compound is applied in an amount ranging from about 5 mg to about 75 g per tree.

8. The method as claimed in claim 1, wherein said pyrazole compound is applied at a coverage in a range of from about 20 mg/10a to about 2,000 g/10a.

* * * * *